(12) United States Patent
Weitzner et al.

(10) Patent No.: US 11,134,830 B2
(45) Date of Patent: Oct. 5, 2021

(54) MEDICAL DEVICE DELIVERY SYSTEM AND METHODS OF USE

(71) Applicant: Boston Scientific Scimed, Inc., Maple Grove, MN (US)

(72) Inventors: Barry Weitzner, Acton, MA (US); Ryan Hartman, Kingston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 918 days.

(21) Appl. No.: 15/848,278

(22) Filed: Dec. 20, 2017

(65) Prior Publication Data

US 2018/0177981 A1    Jun. 28, 2018

Related U.S. Application Data

(60) Provisional application No. 62/439,233, filed on Dec. 27, 2016.

(51) Int. Cl.
*A61B 1/018* (2006.01)
*A61M 25/01* (2006.01)
(Continued)

(52) U.S. Cl.
CPC .......... *A61B 1/018* (2013.01); *A61B 1/0055* (2013.01); *A61B 1/00096* (2013.01);
(Continued)

(58) Field of Classification Search
CPC .......... A61M 25/0147; A61M 25/0133; A61M 25/0116; A61M 25/0152; A61M 25/0155; A61M 25/0172; A61M 25/0194; A61M 25/06; A61M 2025/015; A61M 2025/0161; A61M 2025/0175; A61M 2025/0177; A61M 2025/0197; A61M 2025/0233; A61M 25/01; A61B 17/00234; A61B 2017/00278; A61B 2017/00283;
(Continued)

(56) References Cited

U.S. PATENT DOCUMENTS

| | | | |
|---|---|---|---|
| 5,403,311 A | 4/1995 | Abele et al. | |
| 5,957,919 A * | 9/1999 | Laufer | A61B 18/1492 606/28 |

(Continued)

FOREIGN PATENT DOCUMENTS

EP    3005993 A2    4/2016

OTHER PUBLICATIONS

International Search Report and Written Opinion in PCT/US2017/067528, dated Mar. 21, 2018 (14 pages).

*Primary Examiner* — Ryan N Henderson
*Assistant Examiner* — Pamela F Wu
(74) *Attorney, Agent, or Firm* — Bookoff McAndrews, PLLC

(57) ABSTRACT

Embodiments of the disclosure are drawn to a medical device delivery system. The system may include a shaft having a proximal end and a distal end. The device may also include a visualization system at a distal region of the shaft. The system may further include at least one latching structure configured to extend beyond the distal end of the shaft and retract within the distal region of the shaft and at least one advancement mechanism configured to extend beyond the distal end of the shaft to pull the shaft in a distal direction.

15 Claims, 5 Drawing Sheets

(51) Int. Cl.
- *A61M 25/04* (2006.01)
- *A61M 27/00* (2006.01)
- *A61B 1/005* (2006.01)
- *A61B 1/00* (2006.01)
- *A61B 17/11* (2006.01)
- *A61B 17/00* (2006.01)

(52) U.S. Cl.
CPC .... *A61B 17/00234* (2013.01); *A61B 17/1114* (2013.01); *A61M 25/0138* (2013.01); *A61M 25/0147* (2013.01); *A61M 25/04* (2013.01); *A61M 27/002* (2013.01); *A61B 1/0051* (2013.01); *A61B 1/00156* (2013.01); *A61B 2017/00278* (2013.01); *A61B 2017/00331* (2013.01); *A61B 2017/00349* (2013.01); *A61B 2017/00818* (2013.01); *A61B 2017/1139* (2013.01); *A61M 2025/015* (2013.01)

(58) Field of Classification Search
CPC .. A61B 2017/0034; A61B 2017/00353; A61B 2017/00358; A61B 1/0008; A61B 1/00087; A61B 1/00098; A61B 1/00101; A61B 1/00131; A61B 1/00133; A61B 1/012; A61B 1/018; A61B 1/00082; A61B 1/00156; A61B 1/01; A61B 1/31; A61F 2/958; A61F 2/82
USPC ........................................................ 600/114
See application file for complete search history.

(56) References Cited

U.S. PATENT DOCUMENTS

| | | |
|---|---|---|
| 7,144,401 B2 | 12/2006 | Yamamoto et al. |
| 7,294,139 B1* | 11/2007 | Gengler ............... A61B 17/221 606/113 |
| 2001/0018574 A1 | 8/2001 | Toledo et al. |
| 2002/0161341 A1 | 10/2002 | Stinson et al. |
| 2003/0069533 A1 | 4/2003 | Kakutani et al. |
| 2005/0113716 A1 | 5/2005 | Mueller, Jr. et al. |
| 2005/0272976 A1* | 12/2005 | Tanaka ................. A61B 1/0016 600/114 |
| 2006/0111704 A1 | 5/2006 | Brenneman et al. |
| 2008/0091068 A1 | 4/2008 | Terliuc |
| 2009/0143713 A1* | 6/2009 | Van Dam ............ A61M 27/008 604/9 |
| 2009/0255544 A1* | 10/2009 | Cox .................... A61B 17/0401 128/898 |
| 2010/0168557 A1 | 7/2010 | Deno et al. |
| 2011/0054381 A1 | 3/2011 | Van Dam et al. |
| 2011/0137394 A1* | 6/2011 | Lunsford ............ A61B 17/1114 623/1.11 |
| 2012/0130417 A1 | 5/2012 | Lepulu et al. |
| 2012/0296257 A1 | 11/2012 | Van Dam et al. |
| 2014/0236064 A1* | 8/2014 | Binmoeller ......... A61B 17/1114 604/8 |
| 2014/0309683 A1* | 10/2014 | Bagwell ............. A61B 18/1492 606/207 |
| 2016/0331931 A1 | 11/2016 | Tilson et al. |
| 2016/0338681 A1* | 11/2016 | Smith ................ A61B 1/00089 |

* cited by examiner

MEDICAL DEVICE DELIVERY SYSTEM AND METHODS OF USE

CROSS-REFERENCE TO RELATED APPLICATION(S)

This patent application claims the benefit under 35 U.S.C. § 119 to U.S. Provisional Patent Application No. 62/439,233, filed on Dec. 27, 2016, the entirety of which is incorporated herein by reference.

TECHNICAL FIELD

Aspects of the present disclosure relate generally to methods and systems for guiding and delivering a medical device, and, specifically, to methods and systems for guiding and delivering an implantable device to couple together at least two structures.

INTRODUCTION

Minimally invasive surgery may utilize small incisions or natural orifice entry points to provide access to a surgical site. Minimally invasive approaches may result in faster recovery times, reduced pain, reduced blood loss, and/or less scarring, among other benefits. Recent advancements in technology have allowed physicians to treat pancreatic pseudocysts minimally invasively by creating a connection between the pancreas and the gastrointestinal (GI) tract using a stent to, for example, fluidly connect the pancreas and the GI tract to drain a pancreatic pseudocyst into the GI tract. This technology may be limited, however, to use with adhered anatomical structures or anatomical structures that are in close proximity to one another.

SUMMARY

Embodiments of the present disclosure are directed to an implantable device and delivery system for creating a connection between two spaced-apart anatomical structures. Various embodiments of the disclosure may include one or more of the following aspects.

Aspects of the disclosure are drawn to a medical device delivery system. In accordance with one embodiment, the system may include a shaft having a proximal end, a distal end, and a length extending between the proximal end and the distal end. The shaft may be a steerable catheter. The system may also include a visualization system at a distal region of the shaft. The system may also include at least one latching structure configured to extend beyond the distal end of the shaft and retract within the distal region of the shaft and at least one advancement mechanism configured to extend beyond the distal end of the shaft to pull the shaft in a distal direction.

Various embodiments of the medical device delivery system may include one or more of the following features: the advancement mechanism may include a wheel; the wheel may include at least one grasper projecting from a surface of the wheel; the advancement mechanism may include one or more hooks; the latching structure may include at least one of a hook or a barb; the system may further comprise a stent-delivery system, wherein the medical device delivery system may include a lumen extending from the proximal end to the distal end and dimensioned to receive the stent-delivery system within the lumen; and the system may further comprise a stent-delivery system, wherein the stent-delivery system includes a lumen extending from a proximal end to a distal end that is dimensioned to receive the medical device delivery system within the lumen.

In accordance with another aspect, a method of delivering a medical device may include steering a catheter to within a first anatomical structure of a patient and forming a first opening in a wall of the first anatomical structure. The method may also include advancing the catheter through the first opening so that a distal end of the catheter exits the first anatomical structure, and advancing the catheter to a second anatomical structure of the patient, wherein the second anatomical structure is spaced apart from the first anatomical structure. The method may further include forming a second opening in a wall of the second anatomical structure, guiding a stent-delivery system over, through, or alongside the catheter to the second opening in the wall of the second anatomical structure, and advancing a distal end of the stent-delivery system into the second opening to or through an internal region of the second anatomical structure.

Various aspects of the method may include one or more of the following features: the method may further comprise engaging one or more latching elements extending distally of the distal end of the catheter with the wall of the first anatomical structure before forming the first opening, and engaging the one or more latching elements with the wall of the second anatomical structure before forming the second opening; forming the first opening and forming the second opening may comprise advancing a piercing element through the wall of the first anatomical structure or through the wall of the second anatomical structure, respectively; advancing the catheter to the second anatomical structure may include pulling the distal end of the catheter forward with an advancing mechanism; the advancing mechanism may include at least one of a hook or a wheel; the method may further comprise engaging one or more latching elements extending distally of the distal end of the catheter with the wall of the second anatomical structure and pulling the wall of the second anatomical structure towards the first anatomical structure; the method may further comprise withdrawing the stent-delivery system from the internal region of the second anatomical structure back to the first anatomical structure to deploy a stent contained within the stent-delivery system; the stent-delivery system may contain a stent, and the method may further comprise deploying a distal end of the stent from the stent-delivery system so that the distal end of the stent engages the second opening from within the second anatomical structure; the method may also comprise withdrawing the stent-delivery system from the internal region of the second anatomical structure back to the first anatomical structure and deploying an intermediate portion of the stent from the stent-delivery system as the stent-delivery system is withdrawn from the second anatomical structure to the first anatomical structure; and the method may comprise deploying a proximal end of the stent from the stent-delivery system so that the proximal end of the stent engages the first opening from within the first anatomical structure.

Aspects of the disclosure are also drawn to minimally invasive methods of creating a connection between a first anatomical structure and a second anatomical structure of a patient. The method may include steering a catheter to within a first anatomical structure of a patient, forming a first opening in a wall of the first anatomical structure, and advancing the catheter through the first opening so that a distal end of the catheter exits the first anatomical structure. The method may also include steering the catheter to a second anatomical structure of the patient, wherein the second anatomical structure is spaced apart from the first anatomical structure, forming a second opening in a wall of the second anatomical structure, and guiding a stent-delivery system over, through, or alongside the catheter to the second opening in the wall of the second anatomical structure. The method may further include advancing a distal end of the stent-delivery system into the second opening to an internal region of the second anatomical structure, and deploying a distal end of a stent from the stent-delivery system so that the distal end of the stent engages the second opening from within the second anatomical structure. The method may then include withdrawing the stent-delivery system from the internal region of the second anatomical structure back to the first anatomical structure, deploying an intermediate portion of the stent from the stent-delivery system as the stent-delivery system is withdrawn from the second anatomical structure to the first anatomical structure, and deploying a proximal end of the stent from the stent-delivery system so that the proximal end of the stent engages the first opening from within the first anatomical structure.

Various embodiments of the method may include one or more of the following features: the method may further comprise engaging one or more latching elements extending from the catheter with the wall of the second anatomical structure, and pulling the wall of the second anatomical structure towards the first anatomical structure; and steering the catheter to the second anatomical structure may include pulling the distal end of the catheter forward with an advancing mechanism.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings.

DETAILED DESCRIPTION

Figure 1:
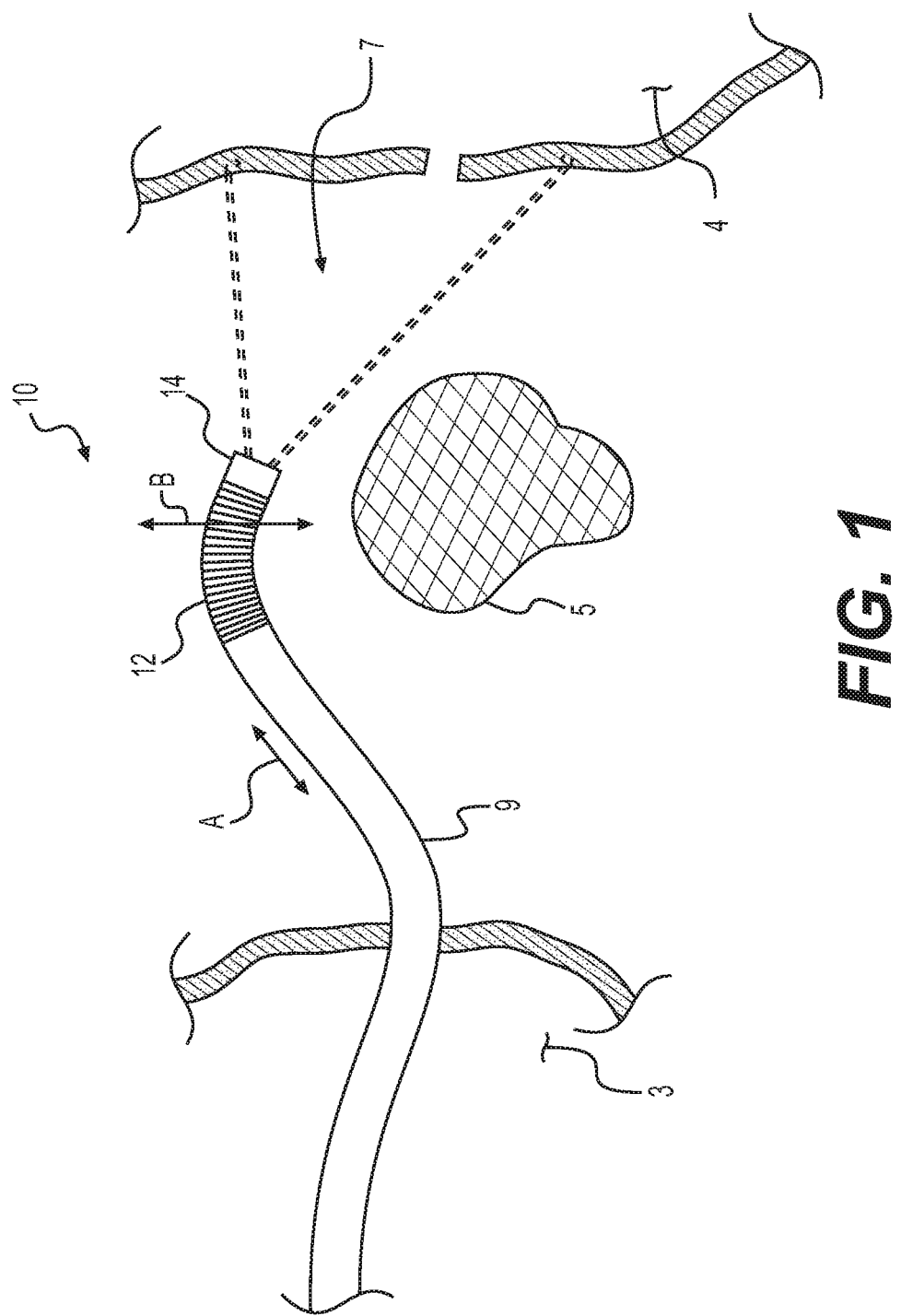
FIG. 1 depicts an exemplary system for coupling two anatomical structures, according to an exemplary aspect of the present disclosure.

Reference will now be made in detail to the exemplary embodiments of the present disclosure described below and illustrated in the accompanying drawings. Wherever possible, the same reference numbers will be used throughout the drawings to refer to same or like parts. The term "proximal" as used herein refers to a position closer to an end of the medical device system that remains outside of the body during use and closer to the operator of the medical device system. The term "distal" refers to an insertion end of the medical device system that is further from the operator of the medical device system during use.

Patients may develop medical conditions that may be treated by creating a connection between two anatomical body structures that are spaced apart from one another. For example, a patient may develop a cyst, or an abscess, a stricture or blockage may develop that interrupts the natural flow of drainage or materials through the body, or fluid may collect in an organ or lumen for any number of reasons. Accordingly, it may be desirable to connect or otherwise couple together two or more anatomical structures (e.g., body lumens or organs) in order to bypass the stricture or blockage and/or to drain the fluid collection or cyst. Other conditions may include, e.g., treatment of cysts or abscesses, thoracic drainage, pericarditis, or other conditions or disease states.

In some instances, however, the structures to be connected may not be adhered to or adjacent to one another. Instead, space may exists between the structures. Available technology may be used if the anatomical structures to be connected are adjacent to or in direct contact with one another and that an opening can be created in one structure to provide access to an outer wall of the next structure, and then an opening may be made in the second structure. A stent may then be fed through the two openings to create an anastomosis between the two adjacent structures.

However, in some implementations, a connection or a coupling may be made between more than two anatomical structures, or to connect or couple anatomical structures that are separated from each other by an intervening space or structure. In such instances, an internal region of a first structure may be accessed via a minimally invasive procedure (e.g., using a catheter or endoscope), and an opening may be made in the wall of the first structure. If the second structure to be connected is not adjacent to or adhered to the first structure, then creating an opening in the first structure may not provide access to the second structure. Instead, a space between the first structure and the second structure may need to be traversed. In some embodiments, intervening structures, e.g., intervening organs, blood vessels, or tissues, may exist between the first structure and the second structure and may need to be navigated around, or dissected away, in order to connect the two structures. In some embodiments, it may also be desirable to draw the first and second structures closer to one another in order to form the connection between them. Embodiments of the disclosure are drawn to methods, systems, and devices that allow for the connection of multiple spaced-apart structures.

FIG. 1 depicts an exemplary system for traversing space between a first structure 3 and a second structure 4 to connect or otherwise couple the two spaced-apart structures. In the embodiment of FIG. 1, a delivery system 10 may be delivered via a minimally invasive procedure to within first structure 1. For example, delivery system 10 may be introduced to an organ or lumen of the GI tract via either the esophagus or the colon of the patient. In some embodiments, structure 3 may be the stomach or duodenum of a patient. In some embodiments, the space between the first and second structures may include a portion of the peritoneal cavity. For example, a connection may be created between the stomach and the gall bladder, or a connection may be created between the gall bladder and the duodenum.

Delivery system 10 may include a flexible, steerable catheter 9 having a proximal end, a distal end, and a length extending from the proximal end to the distal end. One or more lumens may extend through catheter 9. Catheter 9 may include a bending portion 12 capable of moving in two or more degrees of freedom, as indicated by arrow 'B.' In some embodiments bending portion 12 may move up and down, left and right, forward and back, or a combination thereof. Bending portion 12 may be located at a distal region of catheter 9, as is shown in FIG. 1. In some embodiments, bending portion 12 may extend in a proximal direction along a length of catheter 9. In some embodiments, catheter 9 may include a plurality of bending portions 12 extending along its length. Catheter 9 may include one or more control wires (not shown) extending from a distal region to a proximal region of catheter 9 to facilitate bending, navigation, and control of delivery system 10. In some embodiments, forward and back motion may alternatively or additionally be controlled by axial motion of catheter 9.

Delivery system 10 may also include a visualization system 14 to aid in navigating delivery system 10 to first structure 3 or to navigate between first structure 3 and second structure 4 or between or within any other structures. Visualization system 14 may include direct, light-based visualization and/or may include indirect fluoroscopic or ultrasound visualization of delivery system 10. For example, visualization system 14 may include a camera, e.g., an image sensor such as a charge coupled device (CCD), complementary metal oxide semiconductor (CMOS), or any other suitable image sensor, for capturing images at or around a distal region of delivery system 10. Visualization system 14 also may include one or more glass or polymeric lenses for focusing light onto an image sensor. Delivery system 10 may include a lighting device at a distal region to aid in visualization, for example, one or more optical fibers or light-emitting diodes, to create an illuminated field of view 7. Image data and control signals may be transmitted along the length of delivery system 10 via one or more wires or cables, for processing and/or displaying the captured images to the user. One or more wires or cables may extend along the length of delivery system 10 to provide power to visualization system 14, including one or more lighting devices or image sensors. In some embodiments, visualization system 14 may include one or more markers, e.g., a metallic or echogenic material, to improve visibility of delivery system 10 when used with indirect visualization, e.g., fluoroscopic or ultrasonic visualization.

Delivery system 10 may include a proximal control portion (not shown) configured to allow a physician to steer the insertion portion of delivery system 10 to a first structure and from the first structure to one or more additional structures to connect or otherwise couple the structures with one another. The proximal control portion may also include one or more of an illumination source or one or more actuators for controlling the illumination source (e.g., adjusting brightness, focusing, or directing the orientation of the illumination output) and controlling one or more cameras (e.g., focusing, turning on or off, or directing the orientation) that may be located at the distal region.

In some embodiments, as discussed above, delivery system 10 may be inserted into a patient and steered to within a first structure 3. A physician may operate the proximal control portion to push or pull delivery system 10 into place and to bend one or more bending portions 12, e.g., via one or more control wires or any other suitable steering mechanism. A physician may also navigate the delivery system 10 by using visualization system 14, which may also be controlled via the proximal controller. Once in first structure 3, an opening may be made in a wall of the first structure, as will be discussed later in detail, and delivery system 10 may be navigated to exit the opening in structure 3. Using visualization 14 and bending portion 12, delivery system 10 may then be advanced through an intervening space towards second structure 4. Bending portion 12 may be manipulated so as to avoid one or more intervening structures 5 that may lie between the first and second structures.

Figure 2:
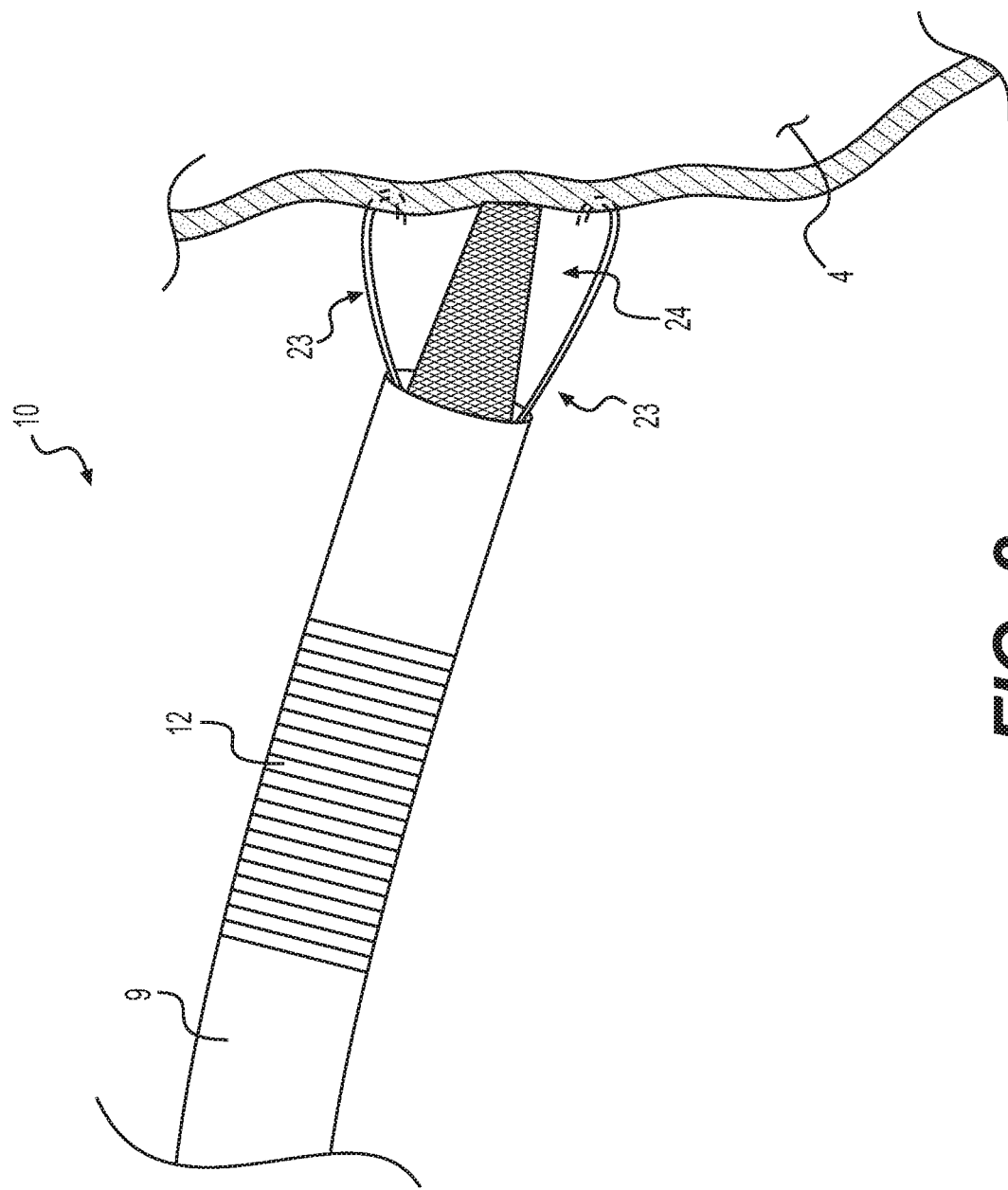
FIG. 2 depicts an exemplary portion of a system for coupling two anatomical structures, according to an exemplary aspect of the present disclosure.

FIG. 2 depicts a distal region of delivery system 10, according to an aspect of the present disclosure. Delivery system 10 may include a piercing element 24 configured to make an opening in one or more anatomical structures. For example, piercing element 24 may include one or more of an electrocautery tip, a needle, a knife, or a bore. In some embodiments, piercing element 24 may be retractable within delivery system 10 so that piercing element 24 may be withdrawn inside of a lumen of steerable catheter 9 when maneuvering delivery system 10 to an anatomical structure (e.g., to a first structure, within a structure, or between structures) to prevent inadvertent damage to surrounding tissues during navigation. When a wall of a structure is reached, piercing element 24 may be extended beyond a distal end of steerable catheter 9 and may protrude from a distal region of delivery system 10. In other embodiments, piercing element 24 may not be retractable and may instead be covered when not in use or may not cause injury to surrounding tissue when not in use (e.g., if an electrocautery tip is used, power may be supplied only during use and not during navigation within or between structures).

When a wall of a relevant structure is reached, piercing element 24 may be positioned adjacent the wall of the structure, and one or both of piercing element 24 and delivery system 10 may be advanced through the wall of the structure. In some aspects, as is shown in FIG. 2, piercing element 24 may have a tapered, e.g., conical or frustoconical, shape to facilitate advancing through the wall of the structure or to enlarge the size of the opening in the wall as piercing element 24 is passed through the wall. In some embodiments, piercing element 24 may have a flat or ovoid profile, may be consistent in width from a proximal end to a distal end, or may be formed as a blade. In some embodiments, piercing element 24 may resemble a Phillips-head screwdriver, may be star-tipped, may have a chisel shape, or may include one or more channels or grooves extending from a distal end to a proximal region of the piercing element. In some embodiments, piercing element 24 may be configured to rotate in order to promote advancement of piercing element 24 through the wall of a structure. In rotating embodiments, piercing element 24 may include, e.g., a threaded portion. Advancement, withdrawal, or rotation of piercing element 24 may be controlled by the proximal control portion of delivery system 10.

The distal region of delivery system 10 may also include one or more latching structures 23 (for example, a structure capable of gripping) configured to hold delivery system 10 in place against the wall of a structure. Latching structures 23 may include hooks, barbs, coils, needles, graspers, a textured surface, or any other suitable mechanism for temporarily affixing, bracing, or steadying the distal end of delivery system 10 to the wall of an anatomical structure. Latching structures 23 in FIG. 2 take the form of hooks. Although two latching structures 23 are depicted, any suitable number of latching structures (e.g., one or more than two) may be included.

In some aspects, one or more latching structures 23 may be configurable to extend beyond and retract within steerable catheter 9. For example, latching structures 23 may be withdrawn inside of steerable catheter 9 when maneuvering delivery system 10 to an anatomical structure (e.g., to a first structure, within a structure, or between two structures) to prevent inadvertent damage to surrounding tissues during navigation. When a wall of a relevant structure is reached, latching structures 23 may be extended beyond a distal end of steerable catheter 9 and may protrude from a distal region of catheter 9 and engage a wall of the structure. In some embodiments, latching structures 23 may engage a wall of the structure before piercing element 24 is extended out of delivery system 10 or advanced though the wall of the structure. In other embodiments, latching structures 23 may engage the wall after piercing element 24 or at the same time as piercing element 24 is extended out of delivery system 10 or advanced though the wall of the structure. Advancement and withdrawal or engagement and release of latching structures 23 may be controlled by the proximal control portion.

In some embodiments, the distal region of delivery system 10 may not include one or more of piercing element 24 or latching structure 23. For example, delivery system 10 may be used in conjunction with a stent-delivery system, which may have its own piercing element or latching structure. In some embodiments, delivery system 10 may be navigated to a first structure, and one or more latching structures 23 may engage a wall of the structure to maintain delivery system 10 in place adjacent a wall of the structure. Any suitable stent-delivery system may be passed coaxially over delivery system 10 or within a lumen of delivery system 10, or, in some embodiments, may be passed alongside delivery system 10. In some embodiments, if the stent-delivery system is to be passed alongside delivery system 10, then delivery system 10 may include a side rail extending along a side of catheter 9, or may have a tubular member extending along a side of catheter 9 forming a lumen for passage of the stent-delivery system. The electrocautery tip of the stent-delivery system, or any other suitable piercing element of the stent-delivery system, may then be advanced distally of delivery system 10 to pierce through the wall of the structure.

Once the opening is formed in the wall of the first structure, latching structures 23 may disengage from the wall of the first structure, and delivery system 10 may be advanced through the opening created in the wall of the first structure 3 and navigated across an intermediate space between the first structure 3 and a second structure 4. One or more latching structures 23 of delivery system 10 may then engage a wall of the second structure 4 and may hold delivery system 10 in place adjacent the wall of a second structure 4. In some embodiments, latching structures 23 may be retracted to pull the wall of the second structure 4 closer to the first structure 3. In some embodiments, delivery system 10 may be pulled proximally in order to pull the wall of the second structure 4 closer to the first structure 3. In other embodiments, latching structures 23 may engage the wall of the second structure 4 without moving the wall of the second structure 4 closer to the wall of the first structure 3. In some embodiments, the stent-delivery system may be advanced with and guided by delivery system 10 from the first structure 3 to the second structure 4, or delivery system 10 may first be guided to the second structure 4, and then the stent-delivery system may be guided over, within, or alongside delivery system 10. Once the stent-delivery system is guided to the second structure 4, a piercing element of the stent-delivery system may be advanced beyond a distal end of delivery system 10 to create an opening within the second structure 4.

In embodiments in which delivery system 10 includes its own piercing element 24, delivery system 10 may be navigated to a region within a first structure 3 and positioned adjacent a wall of the first structure 3. One or both of piercing element 24 and latching structures 23 may be advanced distally of a distal end of steerable catheter 9 (if a retractable embodiment is used). Latching structures 23 may engage a wall of the first structure 3 and may hold delivery system 10 in place adjacent the wall of a first structure 3. Piercing element 24 may be advanced through the wall of the first structure 3 to create an opening in the wall of the first structure 3. Once the opening is formed in the wall of the first structure 3, delivery system 10 may be navigated across an intermediate space between the first structure 3 and a second structure 4. One or more latching structures 23 of delivery system 10 may then engage a wall of the second structure 4 and may hold delivery system 10 in place adjacent the wall of a second structure 4. In some embodiments, latching structures 23 may be retracted to pull the wall of the second structure 4 closer to the first structure 3. In some embodiments, delivery system 10 may be pulled proximally in order to pull the wall of the second structure 4 closer to the first structure 3. In other embodiments, latching structures 23 may engage the wall of the second structure 4 without moving the wall of the second structure 4 closer to the wall of the first structure 3.

Piercing element 24 may then be advanced through the wall of the second structure 4 to create an opening in the wall. Once the opening in the wall of the second structure 4 is formed, then the stent-delivery system may be passed over, through, or alongside of delivery system 10 to the second structure 4. Details of stent deployment will be described further below.

Delivery system 10 may further include one or more advancement mechanisms to assist movement of delivery system 10 between the two structures 3, 4. For example, as shown in the exemplary device of FIG. 3A, delivery system 10 may include one or more hooks 39 and 39'. Hooks 39 and 39' may be configured to retract into and extend distally of catheter 9, as indicated by the arrows in FIG. 3A. As hooks 39 and 39' are retracted, they may pull delivery system 10 forward. The extension and withdrawal of hooks 39 and 39' may allow delivery system 10 to 'crawl' across a surface 30 of an intervening structure, e.g., structure 5 (depicted in FIG. 1), or across a surface of a structure in which an opening will be made to allow delivery system 10 to reach a desired location in which to make the opening in the wall of the structure.

Hooks 39 and 39' may extend and retract at the same time as one another to pull delivery system 10 forward or may extend and retract opposite one another, so that one hook is retracting and pulling delivery system 10 forward as the other hook is extending distally to reengage surface 30 once it has been extended. If hooks 39 and 39' extend and retract in unison, this may pull delivery system 10 forward in a stop-and-go motion. For example, delivery system 10 may not move as hooks 39 and 39' are extended distally, but then may move forward once hooks 39 and 39' reach their distal extension, engage surface 30, and are retracted within catheter 9, pulling delivery system 10 forward. If hooks 39 and 39' are extended and retracted opposite one another, this may create a more consistent pattern of movement. For example, one hook may pull delivery system 10 forward as the other extends, and then the other hook may engage surface 30 and begin pulling delivery system 10 forward as the first hook begins extending distally to reengage surface 30. In some embodiments, pulling only with one of the hooks may steer delivery system 10. For example, pulling with a hook located on the left-hand side of delivery system 10 may steer delivery system 10 to the left, or vice versa. Indeed, pulling repeatedly with the same hook may steer delivery system further and further in one direction.

Figure 3A:
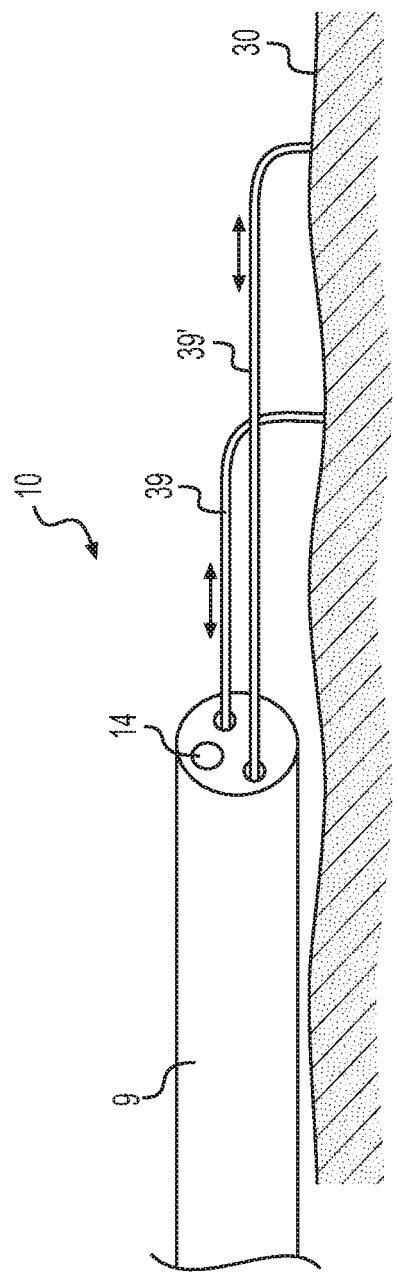
FIG. 3A depicts an exemplary portion of a system for coupling two anatomical structures, according to an exemplary aspect of the present disclosure.

Although two hooks 39 and 39' are depicted in FIG. 3A, delivery system 10 may include a single hook or may include more than two hooks. Additionally, although hooks 39 and 39' are shown as extending proximally and distally along an axis of delivery system 10, in some aspects, one or more hooks may be capable of deflecting off-axis, for example, to pull delivery system 10 upwards, downwards, or to the side, or to engage a portion of surface 30 that may be above, below, at an angle to, or to the side of delivery system 10. Movement of hooks 39 and 39' may be controlled via the proximal control portion of delivery system 10. Visualization system 14 may aid in navigation and may inform control of hooks 39 and 39'.

Figure 3B:
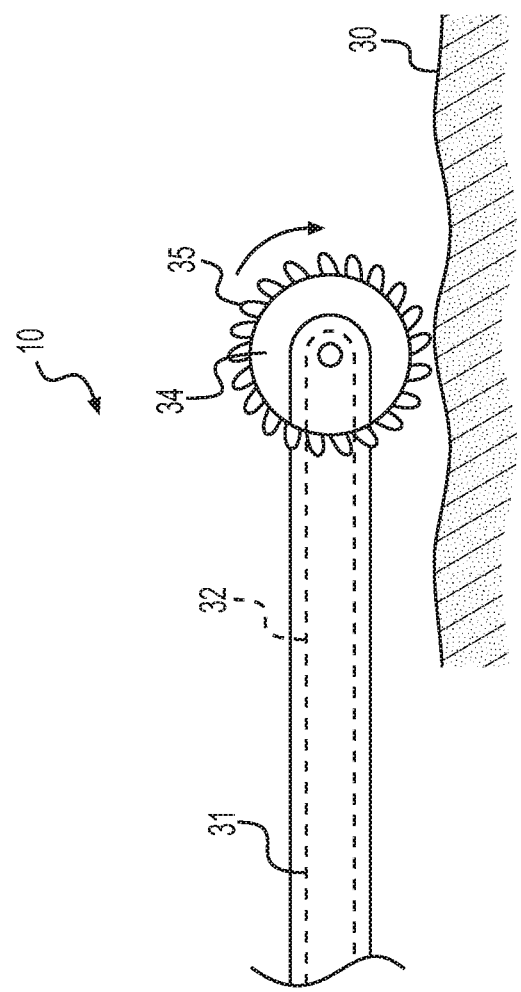
FIG. 3B depicts an exemplary portion of a system for coupling two anatomical structures, according to an exemplary aspect of the present disclosure.

FIG. 3B depicts another exemplary mechanism for advancing delivery system 10. Delivery system 10 may include one or more wheels 34 configured to pull delivery system 10 across surface 30. For example, wheel 34 may include one or more graspers 35 (e.g., a protrusion) projecting from a surface of wheel 34 to help wheel 34 engage (e.g., grip) surface 30. Graspers 35 may include, e.g., one or more of treads, micropatterns, projections, barbs, hooks, needles, bristles, or any suitable structure or combination of structures for engaging tissue. In some aspects, graspers 35 may extend at an angle from a periphery of wheel 34 to help pull delivery system 10 forward as the wheel rotates along surface 30.

Wheel 34 may be mounted on a base 31. In some aspects, base 31 and wheel 34 may be dimensioned to be retractable within catheter 9. For example, base 31 and wheel 34 may retract within a lumen of catheter 9 during navigation of delivery system 10 to the first structure 3 so that wheel 34 does not catch on or injure surrounding tissue. Wheel 34 may then be extended once inside of a first structure 3, e.g., to navigate to a region of the first structure 3 in which to form a first opening in the wall, or in order to pull delivery system 10 across intervening structures located between the two or more structures 3, 4 to be connected to one another. In other embodiments, however, wheel 34 may also be extended distally of catheter 9 to aid in movement or navigation of delivery system 10 when en route to the first structure.

In some aspects, base 31 may be biased towards surface 30 to promote engagement of graspers 35 and wheel 34 with surface 30. In some aspects, base 31 may be capable of deflecting off-axis, for example, to pull delivery system 10 upwards, downwards, or to the side, or to engage a portion of surface 30 that may be above, below, at an angle to, or to the side of delivery system 10. In some embodiments, wheel 34 may be moveably mounted on base 31 so that wheel 31 can be steered to the left, to the right, or straight via a proximal controller.

In embodiments in which multiple wheels 34 are present, each wheel 34 may be mounted on its own base 31, or multiple wheels may be mounted on the same base 31. For example, a base 31 may include wheels 34 mounted on either side of the base or may include wheels 34 mounted along a length of the base on the same or opposite sides.

Movement of wheel 34 may be controlled via the proximal control portion of delivery system 10. One or more drive cables, pulley systems, or control wires or cables may extend a length of delivery system 10 and may control rotation of wheel 34. For example, the delivery system depicted in FIG. 3B includes a drive cable 32 extending along a length of base 31. One or more of these controls may also control movement (e.g., extension and retraction) of base 31 or wheel 34, or separate wires or cables may control movement of base 31.

In some aspects, wheel 34 may be collapsible. For example, wheel 34 may assume a collapsed configuration with retracted within a lumen of catheter 9, e.g., to decrease the size of wheel 34 for storage in the lumen. Upon extension of the wheel from the lumen, wheel 34 may be expandable (e.g., self-expandable) and may assume a substantially circular shape.

As discussed above, delivery system 10 may be inserted into an orifice or an incision of a patient and may be pushed through the body (e.g., through the GI tract) to a first structure 3 within the body. In some aspects, one or more advancement mechanisms, e.g., hooks 39 and 39' or wheels 34, may aid in movement of delivery system 10 to the first structure 3, or, in some aspects, one or more advancement mechanisms may be covered or withdrawn within catheter 9 during navigation of delivery system 10 to the first structure 3. The first structure may be a lumen or an organ.

Once within the first structure 3, delivery system 10 may be operated to create an opening in the wall of the first structure 3, as described above. Delivery system 10 may then be advanced through the opening in the first structure 3 and may then be navigated through an intervening space (e.g., the peritoneal space) between the first structure 3 and a second structure 4. In some aspects, one or more advancement mechanisms, e.g., hooks 39 and 39' or wheels 34, may aid in movement of delivery system 10 from the first structure 3 to the second structure 4 or in the navigation of delivery system 10 around one or more intervening structures. A hole may then be made in the second structure, as described above.

Figure 4:
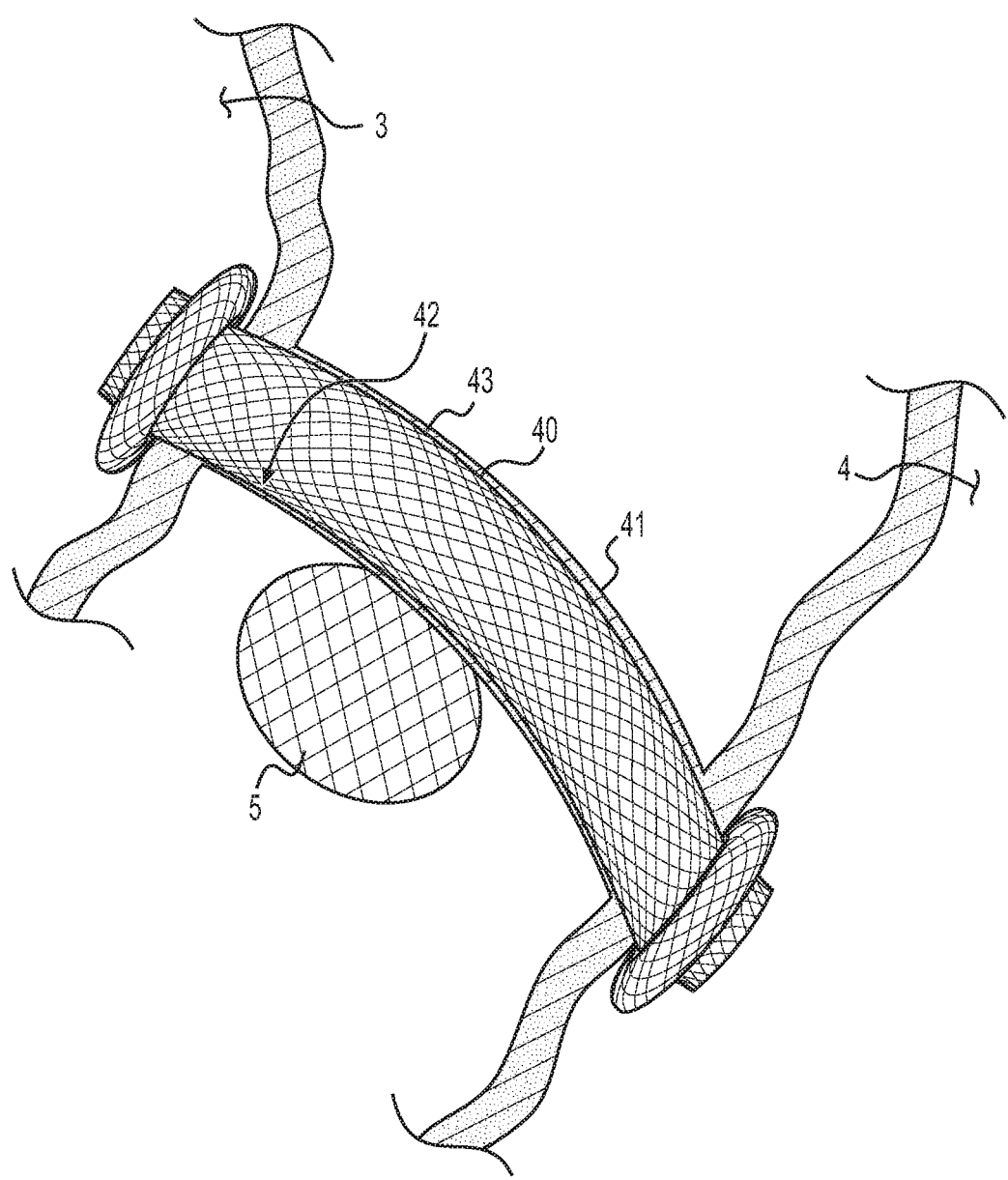
FIG. 4 illustrates an exemplary stent for coupling two anatomical structures, according to an exemplary aspect of the present disclosure.

In some embodiments, delivery system 10 may be used to pull the second structure 4 towards the first structure 3. Pulling the second structure 4 towards the first structure 3 may decrease the amount of space between the structures 3, 4 or may bring the two structures 3, 4 into direct contact with each other, e.g., to align the first and second holes with one another. After the two structures 3, 4 are moved closer to one another, a stent-delivery system may be advanced over, through, or alongside of delivery system 10 to deploy a stent. For example, a stent may have a flange or a broadened portion at each of the proximal and distal ends configured to engage an inner wall of an anatomical structure around the opening in the wall. The stent may also have a narrower intermediate portion configured to extend between the two structures 3, 4. Stent 40 of FIG. 4 shows this configuration.

If first structure 3 and second structure 4 are able to be pulled close to one another or in contact with one another, then a stent 40 with a shorter intermediate portion may be used, since the distance between the two structures would be reduced. Accordingly, a stent 40 would only need to span the distance between the two structures and the thickness of the walls of the first and second structures. In some aspects, it may be possible to use a standard stent or a similar device to connect the first structure 3 and the second structure 4 via the first opening and the second opening if the first and second structures 3, 4 may be brought sufficiently close.

In other embodiments, a stent 40 having a longer intermediate portion may be used, for example, when the first structure 3 and the second structure 4 are spaced further apart from one another, if there are one or more intervening structures 5 in the way preventing second structure 4 from being brought sufficiently close to first structure 3, or if it is not desirable to move the first and second structures 3, 4 closer to one another. An exemplary longer version of stent 40 is shown in FIG. 4. Stent 40 may be long enough to span the walls of first structure 3 and second structure 4, as well as a space between first structure 3 and second structure 4, at least a portion of which may be occupied by an intervening structure 5. In some aspects, first structure 3 and second structure 4 may be spaced several centimeters away from each other, for example, up to 10 centimeters away from each other, up to 15 centimeters away from each other, or up to 20 centimeters away from each other. A longer version of stent 40 may accordingly be long enough to span such exemplary distances.

Stent 40 may be deployed in any suitable manner. For example, in some aspects, delivery system 10 may be navigated to first structure 3, and the stent-delivery system may be guided along (e.g., over, through, or next to) delivery system 10 to the first structure. Once an opening is made in first structure 3 (either with the assistance of the stent-delivery system or without the assistance of the stent-delivery system, as described above), delivery system 10 may traverse a space between the first and second anatomical structures and may make an opening in the second structure 4 (either with the assistance of the stent-delivery system or without the assistance of the stent-delivery system, as described above). In some aspects, delivery system 10 may then be used to pull second structure 4 closer to first structure 3. In other aspects, delivery system 10 may not be used to move second structure 4 closer.

Stent 40 may be sheathed in a collapsed configuration within a capsule, a catheter, or another portion of the stent-delivery system configured to constrain stent 40 into a collapsed configuration for delivery to the first and second structures 3, 4. The portion of the stent-delivery system containing stent 40 may be guided over, within, or alongside of delivery system 10 to a region through the opening of second structure 4 and within second structure 4. A distal end of stent 40 may be released from the stent-delivery system so that a distal flange portion of stent 40 having a wider cross-section than a cross-section of the intermediate portion of stent 40 expands and engages an inside of the wall of second structure 4. The stent-delivery system may then be withdrawn through the opening in second structure 4. If first structure 3 and second structure 4 are closer to or in contact with one another, then the stent-delivery system may be withdrawn through the opening in first structure 3. Once the stent-delivery system is within first structure 3, a proximal end of stent 40 may be released from the stent-delivery system so that a proximal flange portion of stent 40 having a wider cross-section than a cross-section of the intermediate portion of stent 40 expands and engages an inside of the wall of first structure 3. If first structure 3 and second structure 4 are further apart from one another, for example, if there is intervening space or an intervening structure 5, then an intermediate portion of stent 40 may be released from the stent-delivery system as the stent-delivery system is withdrawn from the second structure, across the intermediate space, and into an opening of the first structure. Once within the first structure, deployment of the distal end of stent 40 may proceed as previously described.

Deployment of stent 40 may proceed with delivery system 10 affixed to second structure 4. For example, delivery system 10 may be used to form an opening in the wall of second structure 4 and may be held in place against the wall of second structure 4. The stent-delivery system may be guided to second structure 4 by being passed within, over, alongside delivery system 10. The stent-delivery system may then be inserted into the opening in second structure 4 with delivery system 10 still attached to second structure 4, and delivery system 10 may be used to guide the stent-delivery system as it is withdrawn from second structure 4 back to first structure 3. In some aspects, delivery system 10 may be withdrawn from second structure 4 back to first structure 3 together with the stent-delivery system. In some aspects, delivery system 10 may be withdrawn from second structure 4 back to first structure 3 once the stent-delivery system reaches second structure 4, for example, to make room for the stent-delivery system to access the opening in the second structure 4.

Stent 40 may include one or more coatings. For example, stent 40 may include a coating 42 on an inner surface designed to prevent or reduce tissue ingrowth that may cause restriction in stent 40. For example, coating 42 may include one or more of a silicone, polyurethane, or other suitable stent barriers or bio-absorbable stent barriers. Coating 42 may also prevent fluid being drained from second structure 4 into first structure 3 from being leaked into the intervening space. Thus, coating 42 may be waterproof.

Stent 40 may also include an outer coating 43 designed to promote tissue ingrowth. If the walls of first structure 3 and second structure 4 are close enough to one another, then the walls of the two structures may adhere over time so that the openings between the walls join to form a permanent anastomosis between the two structures. If the walls of first structure 3 and second structure 4 are further apart, however, then the two openings may not naturally grow together to form an anastomosis. Accordingly, stent 40 may include coating 43 on an outer surface designed to promote the growth of tissue 41 along the length of the intermediate portion of stent 40. In this way, tissue 41 may grow along the outside of stent 40 between first structure 3 and second structure 4 and, over time, may form a tissue bridge between the two structures. Coating 43 may include, e.g., one or more of mesh, alginate, or scaffolding.

In some aspects, first structure 3 and second structure 4 may adhere to each other to form a permanent anastomosis, or stent 40 may induce the growth of a tissue bridge between the two structures, as described above. Accordingly, in some aspects, stent 40 may be formed of a bioabsorbable material. The bioabsorbable material may be selected to last long enough for tissue to grow and form a patent anastomosis and then degrade after a suitable amount of time. In some aspects, stent 40 may be removed once an adequate natural tissue connection has been formed. For example, imaging may be used to assess the adequacy of the tissue grown around stent 40, or a fluid (e.g., contrast) observable under visualization (e.g., fluoroscopy, computed tomography, magnetic resonance imaging, or other medical imaging) may be introduced to an area between stent 40 and tissue 41 to assess the patency of the tissue connection. If fluid is seen leaking from tissue 41, stent 40 may be left in place, e.g., permanently or for an additional amount of time. If no fluid is seen leaking from tissue 41, then a minimally invasive procedure may be performed to remove stent 40. In some embodiments, no visualization may be used, and stent 40 may be removed after a certain amount of time.

Figure 5:
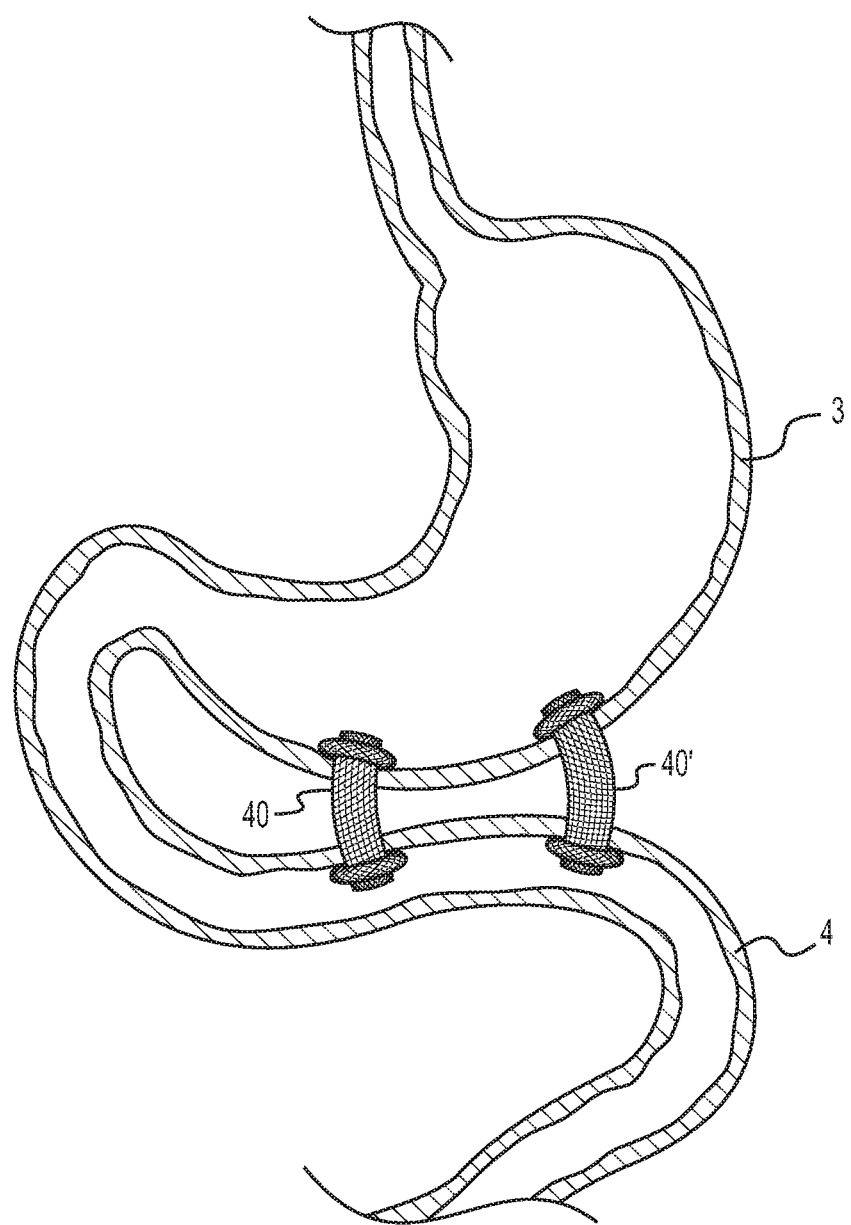
FIG. 5 illustrates an exemplary system coupling a stomach with a jejunum, according to an exemplary aspect of the present disclosure.

In some aspects, as is shown in FIG. 5, multiple stents 40 and 40' may be used to connect a first structure 3 and a second structure 4. Although two stents 40 and 40' are depicted in FIG. 5, more than two stents may also be used. In the embodiment shown in FIG. 5, stents 40 and 40' are used to connect the stomach (first structure 3) with the jejunum (second structure 4) of a patient. Stents 40 and 40' (or any suitable number of stents) may be used to create a communication straight from the stomach to the jejunum so that food may bypass the duodenum. In some aspects, routing food straight from the stomach to the jejunum may improve the outcomes of patients with type 2 diabetes, which may or may not be accompanied by weight loss. In some aspects, using stents 40 and 40' (or any suitable number of stents), may allow for a minimally invasive alternative to open or laparoscopic gastric bypass surgery. For example, the antrum and pylorus may also be closed or otherwise reduced during the minimally invasive procedure, in addition to the placement of stents 40 and 41'.

In other aspects, one or more stents 40 may be used to drain cysts or abscesses, for thoracic drainage, for pericarditis, to bypass strictures or blockages, or for treatment of other conditions or disease states.

In some aspects, three or more anatomical structures may be connected with one another. For example, it may be desirable to connect a first structure with a second structure, but there may be an intervening third structure blocking access to the first and the second structure that cannot be circumvented. In such cases, it may be possible to go through the third structure to gain access to the first and second structures. For example, delivery system 10 may be used to make openings in the third structure and the first structure, and a stent may be placed between the third and first structures to connect the two structures. Delivery system 10 may then be extended through the first structure to another wall of the first structure, and an opening may be made in the other wall of the first structure. Delivery system 10 may then be extended through the other opening in the first structure to the second structure, where an opening may be made in the second structure, and a stent may be placed to connect the first structure and the second structure. Delivery system 10 may be withdrawn from the second structure and the first structure. As delivery system 10 is withdrawn from the first structure, the connection between the first structure and the third structure (e.g., the stent connecting the two structures) may be removed. In this aspect, the connection between the third and first structures may be a temporary one to provide access to allow for the connection of the first and second structures. In some aspects, the openings in the third and first structures that had once connected the two may be closed as delivery system 10 is withdrawn.

In other aspects, however, three or more structures may be more permanently connected to one another. For example, it may be desirable to create a connection between three or more structures.

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A medical device delivery system, comprising:
a steerable catheter having a proximal end and a distal end;
a visualization system at a distal region of the steerable catheter;
at least one latching structure configured to extend beyond the distal end of the steerable catheter and retract within the distal region of the steerable catheter; and
at least one advancement mechanism configured to extend beyond the distal end of the steerable catheter to pull the steerable catheter in a distal direction, wherein the at least one advancement mechanism is extendable from the distal end of the steerable catheter, wherein the at least one advancement mechanism is movable and extendable from the distal end of the steerable catheter separately from the movement and extension of the at least one latching structure from the distal end of the steerable catheter, wherein the advancement mechanism includes at least one wheel, wherein the at least one wheel is rotatable around an axis that is perpendicular to a longitudinal axis of the system, and wherein the at least one wheel is retractable within a lumen of the steerable catheter, and wherein the at least one wheel is collapsible such that the at least one wheel is in a collapsed configuration when retracted within the lumen of the steerable catheter, and such that the at least one wheel expands to a substantially circular shape when extended from the lumen of the steerable catheter.

2. The system of claim 1, wherein the wheel includes at least one grasper projecting from a surface of the wheel.

3. The system of claim 1, wherein the latching structure includes at least one of a hook or a barb.

4. The system of claim 1, further comprising a stent-delivery system, wherein the medical device delivery system includes a lumen extending from the proximal end to the distal end and dimensioned to receive the stent-delivery system within the lumen.

5. The system of claim 1, further comprising a stent-delivery system, wherein the stent-delivery system includes a lumen extending from a proximal end to a distal end that is dimensioned to receive the steerable catheter within the lumen.

6. A medical device delivery system, comprising:
a steerable catheter having a proximal end and a distal end;
at least one latching structure configured to extend beyond the distal end of the steerable catheter and retract within a distal region of the steerable catheter; and
at least one wheel configured to extend beyond the distal end of the steerable catheter to pull the steerable catheter in a distal direction, and wherein the at least one wheel is extendable from the distal end of the steerable catheter separately from the at least one latching structure, wherein the at least one wheel is rotatable around an axis that is perpendicular to a longitudinal axis of the system, and wherein the at least one wheel is retractable within a lumen of the steerable catheter, and wherein the at least one wheel is collapsible such that the at least one wheel is in a collapsed configuration when retracted within the lumen of the steerable catheter, and such that the at least one wheel expands to a substantially circular shape when extended from the lumen of the steerable catheter.

7. The system of claim 6, wherein the at least one wheel includes multiple wheels.

8. The system of claim 7, wherein the multiple wheels are mounted on a base, and wherein the multiple wheels rotate relative to the base.

9. The system of claim 7, wherein the multiple wheels are mounted along a length of a base, and wherein the multiple wheels rotate relative to the base.

10. The system of claim 6, wherein the at least one wheel includes one or more graspers projecting from a surface of the at least one wheel.

11. The system of claim 6, wherein the latching structure includes at least one of a hook or a barb.

12. The system of claim 6, further comprising a stent-delivery system, wherein the stent-delivery system includes a lumen extending from the proximal end to the distal end and dimensioned to receive the steerable catheter within the lumen.

13. A medical device delivery system, comprising:
a steerable catheter having a proximal end and a distal end;
at least one latching structure configured to extend beyond the distal end of the steerable catheter and retract within a distal region of the steerable catheter; and
at least one wheel configured to extend beyond the distal end of the steerable catheter to pull the steerable catheter in a distal direction, wherein the at least one wheel is extendable and retractable from the distal end of the steerable catheter separately from the extension and retraction of the at least one latching structure from the distal end of the steerable catheter, wherein each of the at least one wheel is rotatable around an axis that is perpendicular to a longitudinal axis of the system, and wherein the at least one wheel is retractable within a lumen of the steerable catheter, and wherein the at least one wheel is collapsible such that the at least one wheel is in a collapsed configuration when retracted within the lumen of the steerable catheter, and such that the at least one wheel expands to a substantially circular shape when extended from the lumen of the steerable catheter.

14. The system of claim 13, further comprising a piercing element, wherein the piercing element is extendable and retractable relative to the distal end of the steerable catheter.

15. The system of claim 14, wherein each of the at least one latching structure, the at least one wheel, and the piercing element is separately extendable from the distal end of the steerable catheter.

* * * * *